United States Patent [19]

Petty et al.

[11] Patent Number: 4,503,859

[45] Date of Patent: Mar. 12, 1985

[54] ESOPHAGEAL FUNCTION AND EKG MONITOR

[75] Inventors: Dale H. Petty, Detroit; David A. Penner, West Bloomfield; James A. Van Den Berghe, Madison Heights, all of Mich.

[73] Assignee: William Beaumont Hospital, Royal Oak, Mich.

[21] Appl. No.: 505,146

[22] Filed: Jun. 16, 1983

[51] Int. Cl.[3] .................................... A61B 5/00

[52] U.S. Cl. .................................... 128/635; 128/670; 128/780

[58] Field of Search ............... 128/632, 635, 670, 696, 128/774, 780; 204/403, 433

[56] References Cited

U.S. PATENT DOCUMENTS

| | | | |
|---|---|---|---|
| 3,888,237 | 6/1975 | Mori | 128/635 |
| 4,381,011 | 4/1983 | Somers | 128/635 |
| 4,413,628 | 11/1983 | Tamulis | 128/635 |

FOREIGN PATENT DOCUMENTS

| | | | |
|---|---|---|---|
| 2162656 | 6/1973 | Fed. Rep. of Germany | 128/635 |
| 272477 | 9/1970 | U.S.S.R. | 128/635 |

OTHER PUBLICATIONS

Ask et al., "Combined pH and Press, Measurement Device for Oesophageal Investigations"; *Med. and Biol. Eng. Comput.*, 7-1981, vol. 19, No. 4, pp. 443-446.

Lee et al., "Integrated System for Esophageal pH Monitoring"; *IEEE Engr. in Med. and Biol.*, 10-1979, pp. 53-54.

Sanders et al., "Solid State Portable Gastroesophageal Reflux pH Recorder"; 33rd ACEMB; 10-1980, p. 54.

Falor et al., "24 Hr. Esophageal pH Monitoring by Telemetry"; *Amer. Journ. of Surgery;* vol. 142, 10-1981, pp. 514-516.

"Model 7700 Gastroreflux Data Analyzer"; Del Mar Avionics, 9-1982.

"Model 700 Gastroreflux Recorder"; Del Mar Avionics, 10-1982.

"Flexible pH Electrode for Esophageal and Gastro-Intestinal Research"; Micro-Electrodes, Inc.

"Medilog", Oxford Medical Systems.

"Advertisement for Millar Catheter Pressure Transducers".

*Primary Examiner*—Lee S. Cohen

*Assistant Examiner*—Angela D. Sykes

*Attorney, Agent, or Firm*—Cullen, Sloman, Cantor, Grauer, Scott & Rutherford

[57] ABSTRACT

A monitoring system which records data relating to esophageal acidity fluctuations. The data is recorded on a miniature tape recorder and is then played back and converted to a visually perceptible format. The system has a unique interface circuit for converting the voltage difference between an esophageal probe and a reference electrode into a frequency modulated signal for recording. Another interface circuit reconverts the recorded frequency modulated signal into a voltage for a strip chart recorder. A multi-monitor embodiment is also disclosed which records data relating to esophageal spasms and heart activity in addition to esophageal acidity fluctuations.

16 Claims, 7 Drawing Figures

10
15
17
PH PROBE
16
REF. ELECTRODE.
19
PH AMPLIFIER MODULATOR.
12
20
24 HOUR TAPE RECORDER
24 HOUR RECORDED TAPE.
21
21
23
TAPE PLAYBACK UNIT. HIGH SPEED.
24
DEMODULATOR.
25
PAPER RECORDER.
14
26
24 HR. PAPER RECORD OF ESOPHAGEAL PH.

24 HR. AMBULATORY RECORDING SYSTEM FOR SIMULTANEOUS PH, MANOMETRY AND EKG MONITORING.

ESOPHAGEAL FUNCTION AND EKG MONITOR

BACKGROUND OF THE INVENTION

Field of Invention and Description of Prior Art

The present invention relates to a system for determining the cause of chest pain by monitoring and recording changes in the acidity of a patient's esophageal tract over an extended period of time. A preferred embodiment of the present invention relates to a device for monitoring and recording gastroesophageal pH simultaneously with data related to other causes of chest pain such as esophageal spasms and irregular heart activity.

Gastroesophageal reflux, regurgitating stomach contents into the the esophagus (the passage extending from the pharynx to the stomach), may cause heartburn, chest pain, or difficulty in breathing or swallowing. Monitoring of gastroesophageal reflux has included testing the esophagus for acid sensitivity, measuring the gastroesophageal pressure difference, barium radio-esophagram and perfusion of acid into the stomach with subsequent pH monitoring. All of the above tests have encountered problems and currently monitoring of lower esophageal acidity level, or pH, is considered to be the most reliable technique.

Since gastroesophageal reflux normally occurs on an irregular or sporadic basis it is preferable to develop a history of activity over a prolonged period of time for diagnostic purposes. A monitoring system for recording gastroesophageal reflux incidents preferably records the cycle of regurgitation and clearance. Correlating incidents of gastroesophageal reflux with eating, sleeping and other daily activities provides helpful information to a physician in diagnosing the cause of the gastroesophageal reflux.

In infants, continuous monitoring of gastroesophageal reflux provides an objective method for evaluating the relationship between gastroesophageal reflux and apneic spells associated with Sudden Infant Death Syndrome.

Monitoring a patient at bedside is of only limited value since the patient's activities are severely curtailed which reduces the usefulness of the data collected. One example of such a system is disclosed in the publication entitled "An Integrated System for Esophageal pH Monitoring". Lee, R. J., et al., *IEEE/Engineering in Medicine and Biology Society First Annual Conference*, Session 2, Denver, Colo., (October 1979), pp. 53-54, which describes the use of a large bedside monitor for monitoring esophageal pH, heartrate and repiration of a patient from bedside.

Another system is a portable gastroesophageal reflux pH monitor which periodically records pH reading in a digital memory on discrete CMOS IC's. The discrete readings are later converted into analog data on a chart recorder. An example of one such system is described in the publication entitled "A Solid State Portable Gastroesophageal Reflux pH Recorder", Sanders, G., et al., 33 ACEMB, Washington, D.C., (September–October 1980), p. 54. The primary disadvantage of such a device is that the entire system is useable only for gastroesophageal reflux monitoring and would be a considerable investment for a hospital requiring few gastroesophageal reflux monitoring studies.

Another alternative by which twenty-four hour monitoring of gastroesophageal pH can be accomplished is disclosed in the publication entitled "Twenty-four Hour Esophageal pH Monitoring by Telemetry", by Falor, W. H., et al., *The American Journal of Surgery*, Vol. 142, (October 1981), pp. 514–516. In that system, a battery-powered pH meter and transmitter are worn in a shoulder harness which transmits pH readings to a receiver on a remotely located strip chart recorder. Such a system is effective in monitoring gastroesophageal reflux incidents for extended periods of time but is subject to loss of data caused by radio interference. In addition, the limitation on a patient's activity caused by the need to stay within the range of the receiver make the device inappropriate for persons who normally lead a very active life which would take them out of the range of the receiver.

All of the above disadvantages are overcome by the economical, accurate and efficient gastroesophageal reflux monitor of the present invention.

Another disadvantage of each of the above devices is that they are limited to monitoring GER. Frequently, patients suffering from chest pain may be suffering from spasms of the esophagus, cardiac pain or GER. Previously each of the conditions was separately tested for with separate test equipment. Generally the tests are sequentially performed until the cause for the chest pain was determined. Separately administering the tests is time consuming and therefore delays treatment.

The prior art devices fail to provide a portable combined gastroesophageal reflux monitor, esophageal manometer and EKG monitor which overcomes the disadvantages arising from the need to separately administer the three different tests. Such a device is described herein with reference to the preferred multi-monitor of the present invention.

SUMMARY OF THE INVENTION

Gastroesophageal reflux monitoring according to the present invention is accomplished by properly interfacing known components of electrocardiogram (EKG) equipment with a unique voltage to frequency modulator for recording and a frequency to voltage demodulator circuit for playback. The resultant system is economical, accurate and capable of recording gastroesophageal reflux activity for an extended period of time without limiting a patient's mobility.

Briefly, in the system of the present invention, a pH electrode on a flexible cable is interfaced with a miniature tape recorder for recording changes in acidity in a patient's gastroesophageal tract for an extended period, such as twenty-four hours. The tape is then scanned at a high speed, such as 120 times the recording speed, and is interfaced with a strip chart recorder which produces a compressed readable record of gastroesophageal reflux activity.

More specifically, the interface between the pH electrode and the miniature tape recorder is a unique amplifier/frequency modulator which converts the change in output voltage of the pH electrode into a change in frequency suitable for recording on the magnetic tape in the tape recorder. The recorded frequency modulated signal is then picked up by the scanner and converted by a second interface unit from a variable frequency to a variable voltage which is compatible with standard paper strip chart recorders.

The improved gastroesophageal reflux monitor system of this invention has an electrical sensor, or pH probe, which is placed in a person's esophagus to sense the acidity in the esophagus by sending a variable voltage related to the sensed acidity. A skin electrode provides a reference voltage for measurement of the voltage output of the pH probe. The voltage difference between the pH probe and skin electrode is amplified in a first amplifier which includes a variable resistance feedback loop used to calibrate the system to a relatively acidic solution of known acidity. The output of the first amplifier is connected to a second amplifier which includes a variable resistance input for calibrating the system to a neutral, or low acidity solution of known acidity. The voltage output of the second amplifier is converted in a voltage to frequency convertor to a frequency which varies based upon the amount of voltage received from the second amplifier. The frequency modulated signal received from the voltage to frequency convertor is recorded by a recording device on a magnetic tape over an extended period of time. The magnetic tape is then played back on a scanner which reproduces the signal output of the voltage to frequency convertor. The frequency modulated signal received from the scanner is processed by an amplifier and signal conditioner and then converted back to a variable voltage by a frequency to voltage convertor. The voltage output of the frequency to voltage convertor is amplified in an output amplifier which is adjustable to provide an acceptable level of output voltage for a strip chart recorder, which in turn writes a visually perceptible history of the changes in acidity sensed in a person's esophagus on a paper strip chart.

In a preferred embodiment of the present invention, two modulator outputs are provided; a first for calibrating the unit, and a second for recording data on magnetic tape at a reduced frequency. The same demodulator can thus be used for both real time calibration, and high speed playback of the tape. The degree of reduction and speed of playback are preset to produce a scanner output substantially similar to the frequency of the voltage to frequency convertor.

In another preferred embodiment of the present invention, terminals are provided on the demodulator to allow interconnection of a digital voltmeter for generating an on-line reading for calibrating the system. In this way, the monitor may be calibrated quickly and easily without using the recording device or scanner.

The gastroesophageal reflux monitor of the present invention includes components of known hospital monitoring equipment which are specially interfaced to provide an inexpensive, reliable monitor for continuous monitoring of gastroesophageal reflux activity.

In a preferred multi-monitor embodiment of the present invention a single monitor is provided that would continuously and simultaneously collect data on changes in esophageal pH, esophageal pressure and electrocardiogram activity. The data would be recorded on different channels of a magnetic tape recorder. A synergistic effect of the system being that three primary causes of chest pain can be monitored at the same time by the same monitoring system which allows cross checking and correlation of the data. The patient must only be fitted with the system one time and analysis of all of the data can be performed at an earlier time.

The preferred multi-monitor embodiment is attached to a dual cable and includes a pH probe attached to one cable and a strain gauge, or manometer probe, attached to a second cable. An EKG chest electrode or esophageal EKG probe may also be connected to the monitor by another cable to provide data on heart activity.

The monitor of the present invention permits monitoring of a patient in the course of normal daily activities. When using the monitor there is no need for a patient to be confined to bed or a limited area as is required with bedside console monitors having a telemetry link.

DETAILED DESCRIPTION

Figure 1:
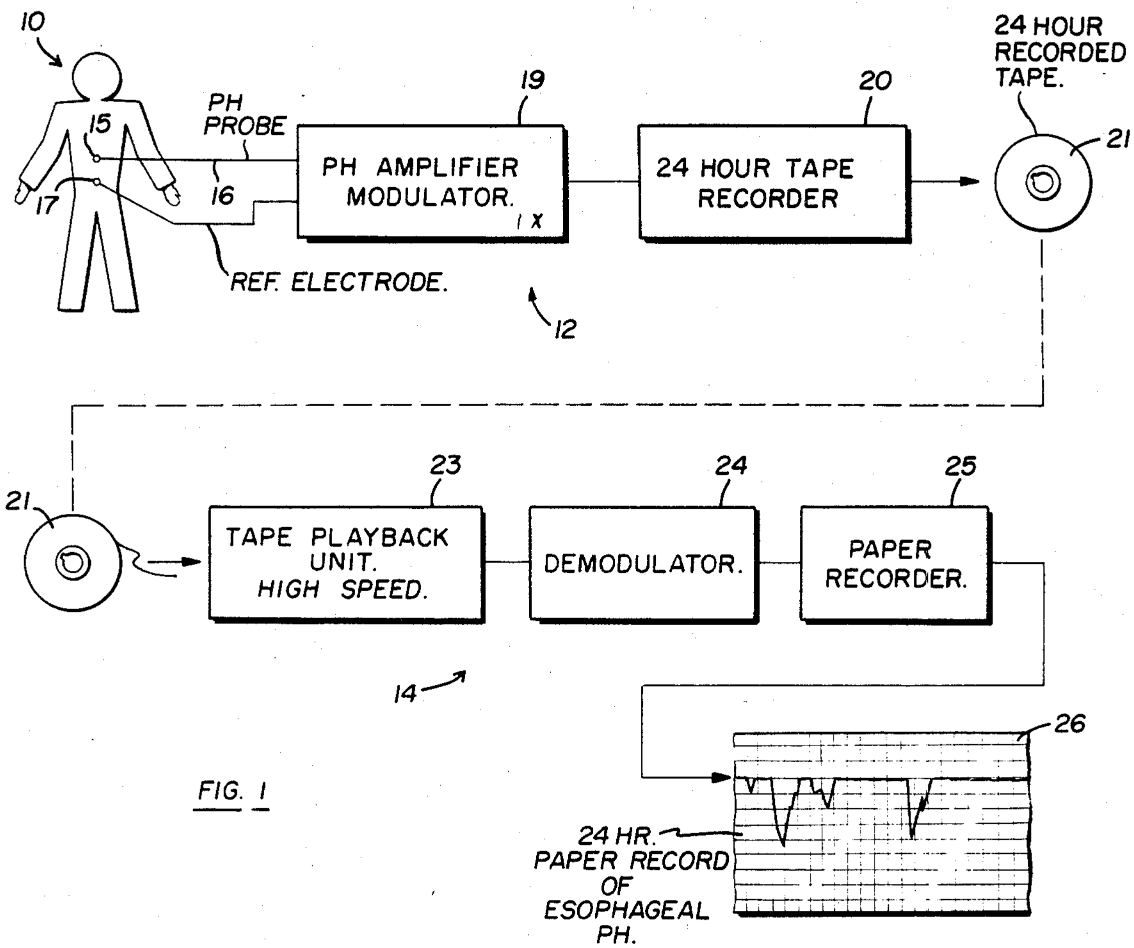
FIG. 1 is a schematic representation of the gastroesphageal reflux monitor of the present invention including both the recording and playback functions of the present invention.

Referring to FIG. 1, a gastroesophageal reflux (GER) monitoring system 10 is shown to comprise a recording system 12 and an interpreting system 14.

The recording system 12 includes a pH electrode 15 which is located in a patient's esophagus, approximately five centimeters above the esophageal sphincter. The pH electrode 15 is connected to the system by means of a flexible cable 16. For example, a flexible pH electrode manufactured by Microelectrodes, Inc., No. MI-506, may be used. A reference electrode 17 is also provided to complete the measurement path between the patient and the monitor 10. The pH electrode 15 and reference electrode 17 are both connected to an amplifier/frequency modulator unit 19 which amplifies the voltage difference between the pH electrode 15 and the reference electrode 17 and then converts the voltage reading to a correlated frequency modulated signal for recording on the tape recorder 20. The amplifier/frequency modulator unit 19 of the present invention provides a unique interface between the pH and reference electrodes 15 and 17 and the tape recorder 20.

The output of the amplifier/frequency modulator unit 19 is received by the miniature tape recorder 20 which records the frequencies on a magnetic tape. A "Mini-Holter Recorder" manufactured by DelMar Avionics is one such unit which is specially designed for ambulatory monitoring on a continuous basis for twenty-four hours. The "Mini-Holter Recorder" is normally used for electrocardiogram monitoring, but is converted to GER monitoring by the use of the amplifier/frequency modulator unit of the present invention. The tape is preferably a magnetic tape having sufficient tape to record a twenty-four hour period.

After the recording is complete, the twenty-four hour recorded tape 21 is scanned by the use of a high speed tape playback unit, which preferably operates at 120 times the speed of recording so that the playback time is kept at a minimum. In this way one tape scanner unit 23 may be used to service many GER monitoring units and/or EKG recorders. This is an important advantage since the recorders normally are much less expensive than the tape scanners. Many modern hospitals are presently equipped with a suitable tape scanner for EKG testing.

The output of the tape scanner 23 is coupled to a demodulator 24 which converts the recorded frequency modulated signal to a corresponding voltage and conditions the voltage signal by suitable amplifiers and filters prior to driving a strip chart recorder 25. The demodulator unit 24 of the present invention provides a unique interface between the tape scanner 23 and the strip chart recorder 25. The strip chart recorder 25 creates a strip chart 26 on a paper tape which may be read by the treating physician in diagnosing the cause of the gastroesophageal reflux in a patient.

Figure 2:
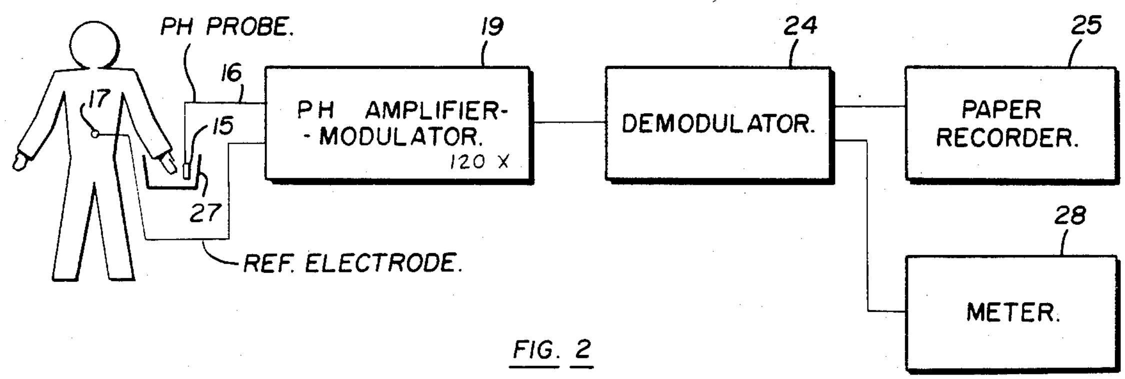
FIG. 2 is a schematic representation of the present invention in the calibration mode.

The present system is calibrated, as shown in FIG. 2, by placing the pH electrode and the patient's finger into a container 27 containing a buffer solution of known pH. The reference electrode 17 is placed on the skin of a patient. Generally, a buffer solution of pH 4 and a buffer solution of pH 7 are used to calibrate the system. The probes are connected to the amplifier/frequency modulator unit 19, and paper recorder 25 or electrical meter 28 for immediate readout. The amplifier/frequency modulator unit 19 is provided with adjustment means as described below, for calibrating the system in accordance with the known buffer solution. The system is calibrated for pH 4 and pH 7 which correspond to points within the range of acidity levels normally found in the esophagus. After the system have been calibrated it is ready for use as previously described.

Figure 3:
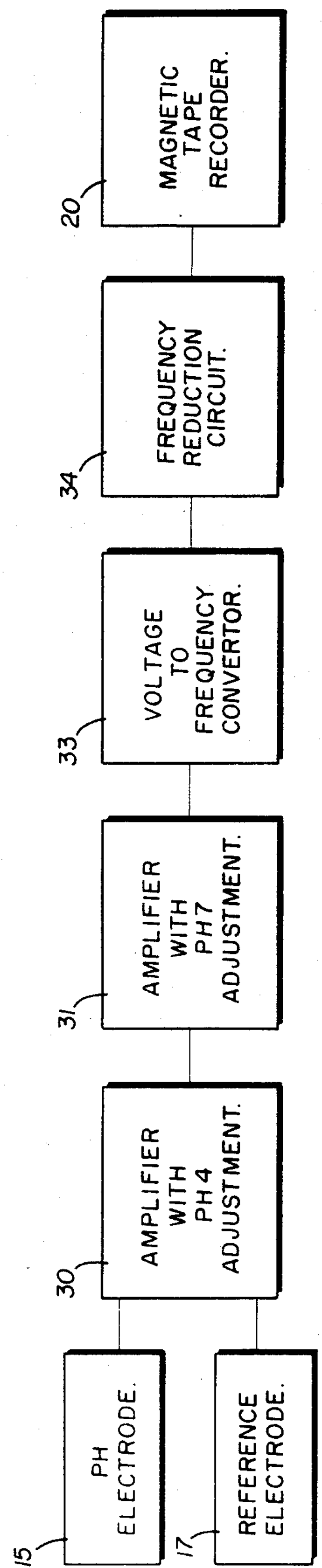
FIG. 3 is a block diagram illustrating the interface circuit of the present invention used to interface from the electrode to the magnetic tape recorder.

As shown in FIG. 3, the general operation of the circuit will be explained in greater detail. The pH electrode 15 and reference electrode 17 both are connected to a first amplifier 30 which is provided to produce a variable gain of from 1.1 to 1.5. The first amplifier 30 is provided with a means for calibrating the high acidity or pH 4 reading of the probe to correspond with a solution having a known pH 4 acidity level. The output of the first amplifier 30 is supplied to a second amplifier 31 which provides further gain of 4.5 for the signal and includes means for adjusting the output to correspond to the proper reading for a neutral, pH 7, solution. The output of the second amplifier 31 is supplied to a voltage to frequency convertor 33 which converts the amplified voltage reading received from the pH electrode to a corresponding frequency modulated signal. The output of the voltage to frequency convertor 33 is then supplied to a frequency reduction circuit which reduces the frequency of the signal received from the voltage to frequency convertor 33 a predetermined amount prior to supplying the frequency to the magnetic tape recorder 20. In a preferred embodiment, the output is at a level of 3 millivolts and at frequencies ranging from 10 to 45 hertz to be compatible with standard EKG monitor/recorders such as the "Mini-Holter Recorder".

Figure 4:
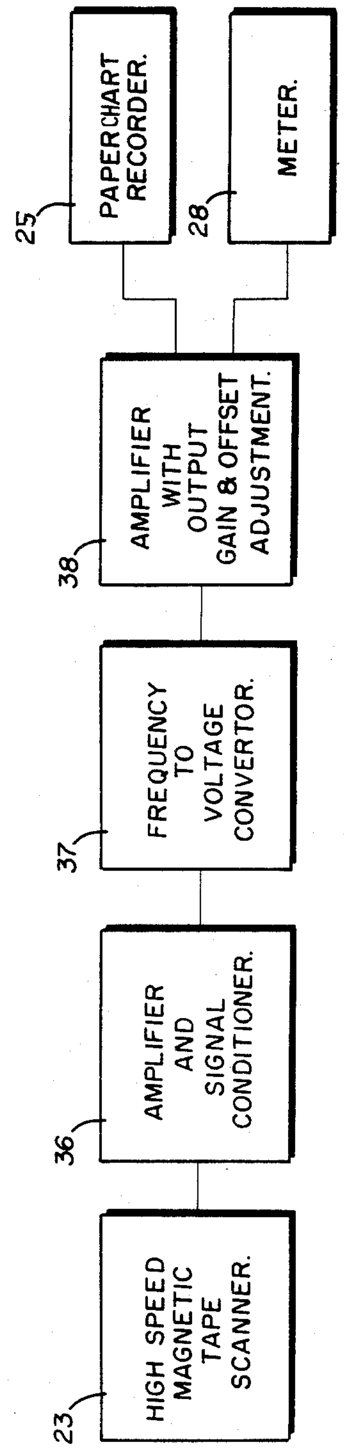
FIG. 4 is a block diagram of the interface between the high speed magnetic tape scanner and the paper strip chart recorder or meter.

As shown in FIG. 4, the general circuit layout for the demodulator is shown in block diagram form. The magnetic tape 21 is played back on a high speed magnetic tape scanner 23. The tape scanner 23 should be operated at a speed matched to the reduction caused by the frequency reduction circuit 34 so that the output supplied to the amplifier and signal conditioner 36 is substantially the same as the output of the voltage to frequency convertor 33. The amplifier and signal conditioner 36 amplify the strength of the signal received from the tape scanner 23 and condition the signal to remove noise outside the signal bandwidth. The output of the amplifier and signal conditioner 36 is supplied to a frequency to voltage convertor 37 which demodulates the signal into a voltage which is further conditioned by the fourth amplifier 38 which is provided with output gain and offset adjustment. The output of the fourth amplifier 38 is recorded on a paper strip chart recorder 25 to allow a treating physician to study the GER activity during the twenty-four hour monitoring period. During calibration, a meter 28 can be used, instead of the paper strip chart recorder 25.

In the disclosed embodiment, the output of the fourth amplifier 38 to the paper strip chart recorder 25 is calibrated for 0.25 volts per pH unit. The alternative output for the meter 28 is preferably 0.1 volts per pH unit to provide units which can be conveniently interpreted.

Figures 5, 6:
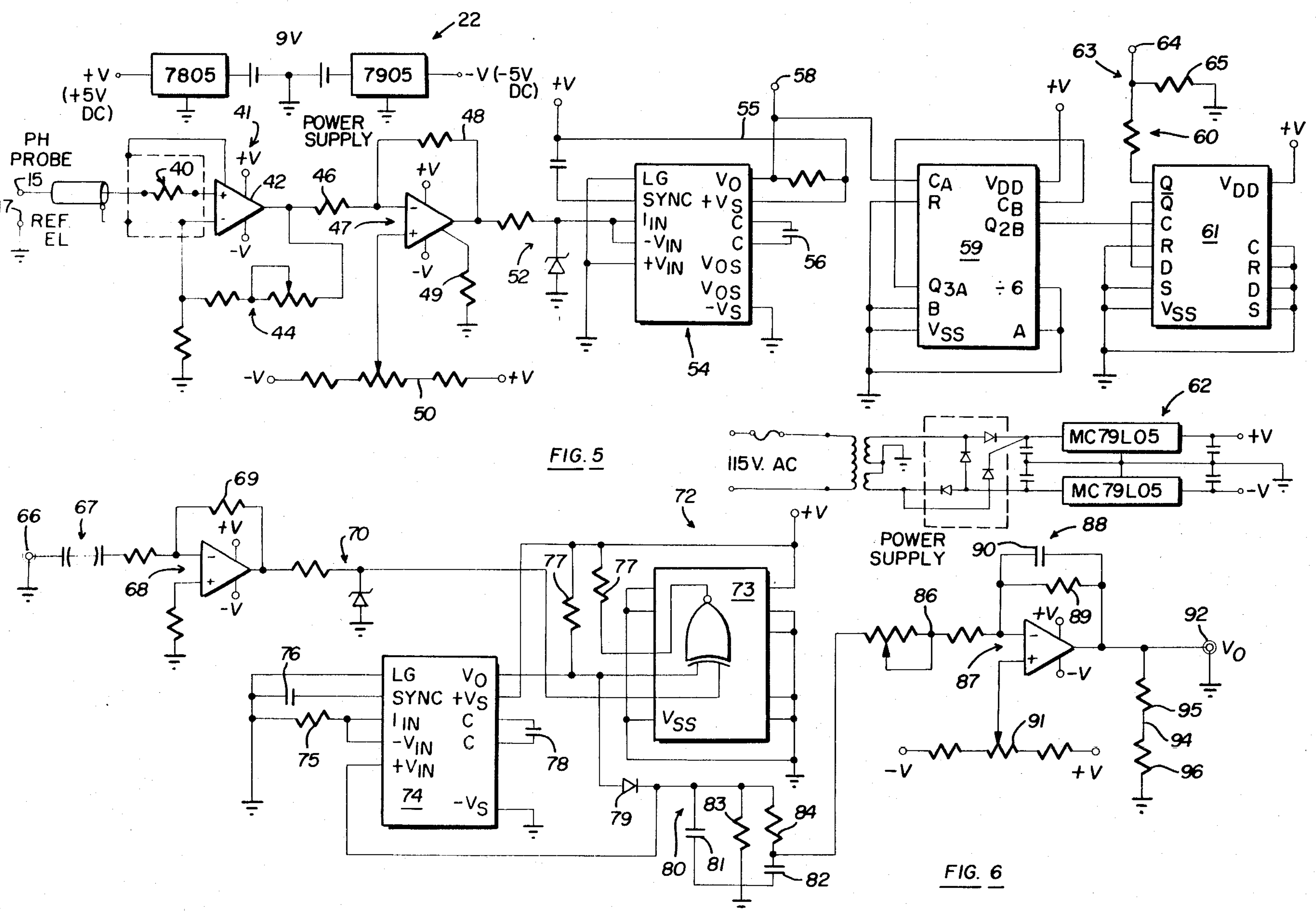
FIG. 5 is a circuit diagram of the amplifier/modulator interfacing the electrode to the magnetic tape recorder.
FIG. 6 is an electrical diagram of the demodulator interfacing the magnetic tape scanner to the paper strip chart recorder.

Referring next to FIG. 5, the circuit of the amplifier/-frequency modulator unit 19 will now be explained. A special power supply 22 is used to provide a stable source of power for the amplifier/frequency modulator unit 19.

The pH electrode 15 is connected through a 100 Kohm resistor 40 to the non-inverting input of an operational amplifier (op amp) 41. The resistor 40 is provided for overload protection of the operational amplifier 41.

The reference electrode is connected to circuit common. The inverting input of op amp 41 is connected to a guard ring around the input leads, the op amp case, and the shield around the pH electrode cable to reduce both stray leakage from the input lead and also noise pick-up. The op amp 41 is an AD515 FET-input operational amplifier specially adapted for use in precision, low-power electrometer applications. A feedback loop 44 is provided from the output of the op amp 41 to the inverting input and includes a variable resistance network that may be a 100 Kohm variable resistor and a 22 Kohm resistor in series which is grounded through a 220 Kohm resistor. The 100 Kohm adjustable resistor is provided to permit the gain of operational amplifier 41 to be adjusted when the probe is placed in a pH 4 solution to calibrate the system.

The output of the operational amplifier 41 is supplied through a 22 Kohm resistor 46 to operational amplifier 47 which is provided for additional gain and to allow calibrating the system to the pH 7 solution. Op amp 47 may be a LM4250 amplifier arranged in the inverting mode and having a 100 Kohm resistor 48 in the feedback loop to provide a gain in the amplifier. A 10 Mohm resistor 49 is provided to limit the power requirements of the op amp 47 to minimum levels. The non-inverting pin of the op amp 47 is attached to a 50 Kohm potentiometer 50 in series with two 330 Kohm resistors for adjusting the system zero offset based upon a solution of pH 7.

The output of op amp 47 passes through a signal clamp 52 which includes a 3.9 Kohm resistor and a grounded diode which may be a 1N5713 zener diode.

After passing through the signal clamp 52 the signal is then input into voltage to frequency (V-F) convertor 54 which converts the signal into a variable frequency signal depending upon the level of the voltage received. The V-F convertor may be a Ad537 integrated circuit which is a monolithic V-F convertor consisting of an input amplifier, a precision oscillator system, an accurate internal reference generator and a high current output stage. V-F convertor 54 is provided with a 4.7 Kohm output pull up resistor, and 0.047 microfarad capacitor for noise reduction. The capacitor 56 is provided to control conversion gain of the integrated circuit, in conjunction with the 3.9 Kohm resistor of signal clamp 52.

The output of the V-F convertor 54 is connected to a terminal 58 which permits takeoff of a high frequency output (120 times recording frequency) for calibration of the system.

The output of the V-F converter 54 is also connected to an industrial time-base generator 59 which divides the frequency by a predetermined amount. The industrial time-base generator 59 may be a MC14566 integrated circuit which is adapted to divide the frequency by 60.

The output of the industrial time-base generator 59 is connected to a flip flop integrated circuit 61 to permit further reduction of the frequency. The flip-flop 61 may be a MC14013 integrated circuit which is capable of reducing the frequency by two to create a total frequency reduction of 120 in the frequency reduction circuit 34 when combined with the industrial time base generator MC14566. It should be realized that other frequency reduction ratios may be used depending upon the rate of tape playback scanning.

The output of the frequency reduction circuit 34 passes through a resistor network 63 for attenuating the signal before passing it to the output terminal 64. The resistor network 63 may include a 2.2 Mohm resistor 60 and a 1 Kohm resistor 65 connected to ground. The output terminal 64 is adapted to be connected to the tape recorder 20 which records the output of the amplifier/frequency modulator unit 19 continuously over an extended period of time.

Referring now to FIG. 6, the circuit of the frequency demodulator 24 is shown in detail. The power supply for the demodulator is shown in FIG. 6.

The frequency demodulator 24 receives an input from the tape scanner 23 at the coaxial terminal 66. The input is then filtered through a capacitor resistor network 67 which may include two oppositely oriented 0.22 microfarad capacitors and a 4.7 Kohm resistor connected in series which are adapted to filter unwanted noise from the circuit.

The input is then supplied to the inverting terminal of the op amp 68 which may be a LM318 op amp. The operational amplifier 68 is provided with a feedback loop 69 having a 100 Kohm resistor for signal amplification and is connected to ground on its non-inverting input through a 4.7 Kohm resistor.

The output of op amp-68 is supplied to a signal clamp 70 which may comprise a 2.7 Kohm resistor and a grounded zener diode which may be a 1N5713 diode.

The output of the signal clamp 70 is then connected to a frequency to voltage convertor network 72 which includes an exclusive NOR gate integrated circuit 73 and a voltage to frequency convertor 74. In the disclosed embodiment, the exclusive NOR gate integrated circuit is a 74LS266 integrated circuit and the convertor is an AD537 integrated circuit. The input of the convertor 74 includes a resistor 75 for convertor gain and may be a 6.8 Kohm resistor. Capacitor 78 is used to set the convertor gain and may be a 0.001 microfarad capacitor. The convertor 74 also includes a capacitor 76 for noise filtering which may be a 0.047 microfarad capacitor. A resistor network 77 two 10 Kohm resistors if provided for output pull up purposes.

The output of the resistors and the exclusive NOR gate integrated circuit are fed through a diode 79 which may be a 1N914 diode whose output is fed back to the convertor 74 and also goes to the filter network 80. The filter network 80 includes two capacitors 81 and 82 and may be 0.0025 and 0.22 microfarad capacitors, respectively. The capacitors 81 and 82 are interconnected with resistors 83 and 84 which are 4.7 and 15 Kohm resistors, in the disclosed circuit.

The output of the filter network 80 passes through the resistor network 86 prior to being supplied to op amp 87. The resistor network 86 may include a 50 Kohm variable resistor in series with a 68 Kohm resistor. The op amp 87 is provided for additional gain and includes a feedback loop 88 comprising a resistor 89 and capacitor 90 for filtering purposes. The resistor 89 may be a 470 Kohm resistor and the capacitor is preferably a 0.01 microfarad capacitor. The input from the filter network 80 is connected to the inverting input of the op amp 87 while the non-inverting input is connected to a resistor network which may include a 20 Kohm potentiometer in series with an 82 Kohm and 68 Kohm resistor for adjusting of the offset of the op amp 87. In the disclosed circuit the op amp 87 is an LM741 integrated circuit.

The output of the op amp 87, is supplied to a coaxial output terminal 92 which is adapted to be connected to the strip chart recorder 25. An alternative output of the op amp 87 is a meter terminal 94 which is connected at a junction between resistors 95 and 96 which may be 15 Kohm and 10 Kohm resistors, respectively, connected to ground in series for providing a reduced voltage output for connection of a electronic meter 28.

In operation, the gastroesophageal reflux monitor system is first calibrated with the monitor in the calibration mode wherein the output of the voltage to frequency convertor 54 is directly connected to the demodulator 24. The skin reference electrode 17 is attached to the patient's skin and the pH electrode 15 and patient's finger are held in a reference solution having a known pH of 7. The system is then set to yield an output reading of pH 7 on the paper recorder 25 or the meter 28 by adjusting the potentiometer 50. Next the patient's finger and pH electrode 15 are placed in a solution having a pH of 4, and the system is calibrated to provide an output of pH 4 by adjusting the variable resistance network 44 of the op amp 41.

After calibration, the pH electrode is inserted through the patient's nose and into the esophagus to a location approximately five centimeters above the distal esophageal sphincter. The monitor system is then switched on to record the gastroesophageal reflux activity of the patient for twenty-four hours.

Gastroesophageal relux is sensed by the pH electrode since reflux incidents cause the acidity level in a patient's lower esophagus to increase temporarily. In time, the acidity level is reduced after a reflux incident by a gradual clearing of refluxed gastric juices.

Gastroesophageal reflux activity is sensed by the pH electrode sending a voltage, which is related to the sensed acidity, to the two stage amplifier used in calibrating the system. The amplified voltage is then converted into a related frequency modulated signal in a voltage to frequency convertor for recording on a magnetic tape. If a high speed scanner is to be used, two outputs may be provided, one for real-time calibration of the system through the demodulator and paper strip chart recorder or meter, and another output at a reduced frequency for recording a magnetic tape for high speed playback.

After the tape has been completely recorded, preferably over a twenty-four hour period, the system may be removed from the patient and the tape played back on a scanner 23. The scanner 23 preferably operates at a high speed to reduce the time required to analyze each twenty-four hour tape to thereby allow many tapes to be analyzed on a single scanner. The frequency modulated signal received from the tape scanner 23 is converted in the frequency to voltage modulator 24 into a corresponding variable voltage, which is input into the strip chart recorder 25. The strip chart recorder generates a permanent record of esophageal pH which may be visually reviewed by a treating physician in making his diagnosis. By analyzing the continuous history of gastroesophageal reflux and clearing in the ambulant patient valuable diagnostic information relating to the duration, severity and time of occurrence may be obtained.

It will be readily appreciated that the unique amplifier/frequency modulator is a compact and inexpensive piece of equipment. The amplifier/frequency modulator, demodulator and pH electrode are the only new pieces of equipment required at modern hospitals which typically have tape recorders, scanners and strip chart recorders available for other diagnostic tests, to permit continuous ambulatory recording of gastroesophageal reflux. The unique demodulator unit of the present invention interfaces a conventional EKG scanner to a conventional strip chart recorder to generate a paper chart record of gastroesophageal reflux for the monitored time period.

Figure 7:
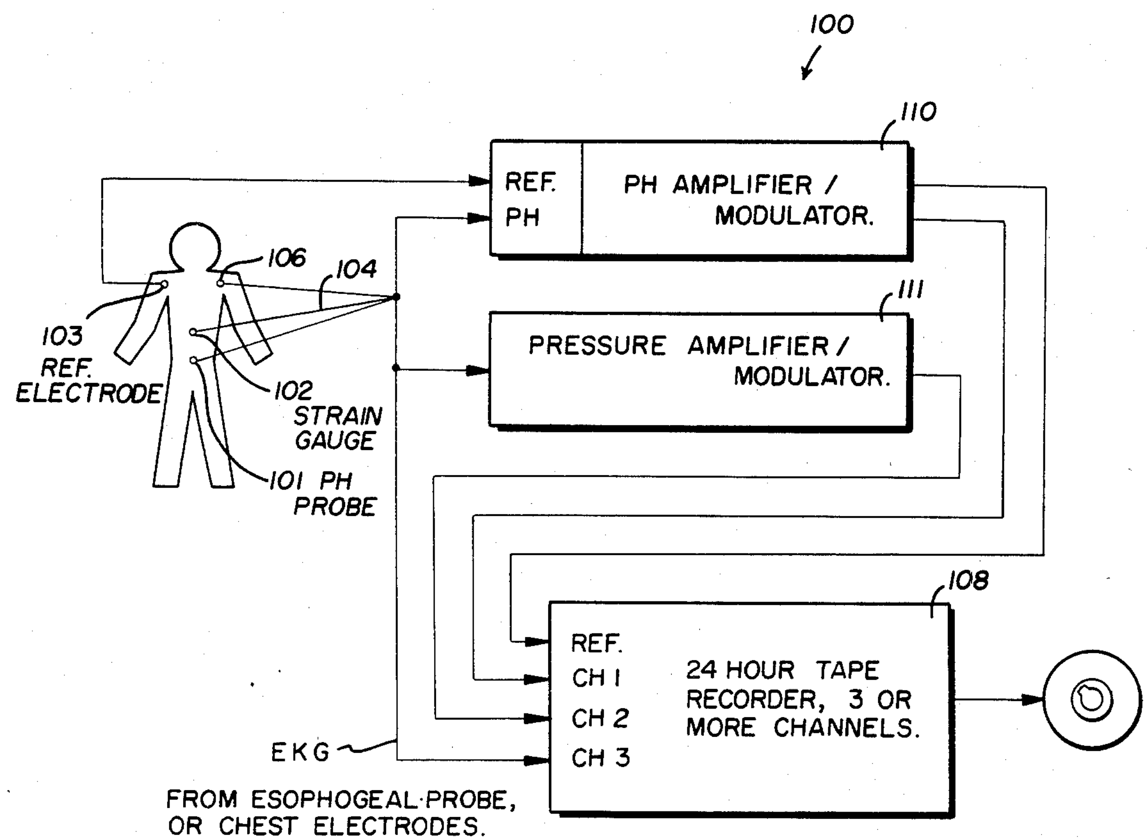
FIG. 7 is a schematic representation of the multimonitor of the present invention including a multiple channel input and output system for monitoring and analysis of esophageal pH, esophageal pressure, and EKG activity.
Figure 7:
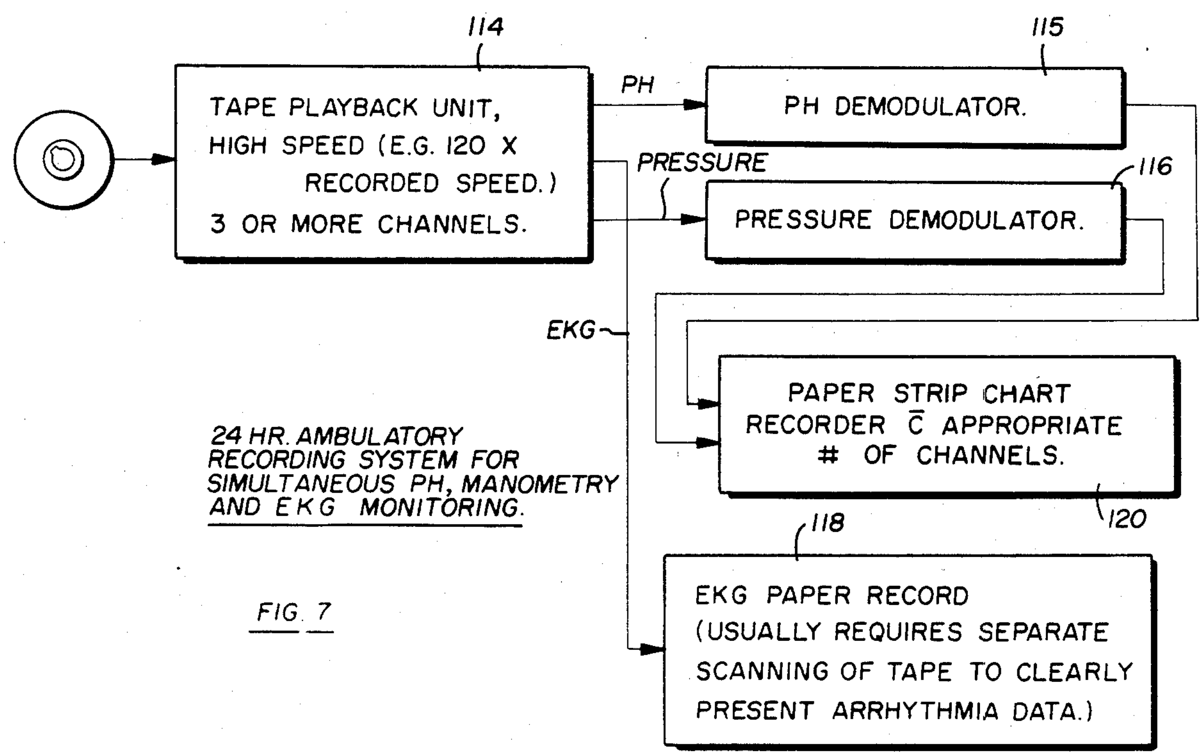

Referring now to FIG. 7, a multiple function chest pain monitor 100 is shown in block diagram form. The multiple function chest pain monitor expands upon the concept of the gastroesophageal reflux monitor described above by adding a probe for measuring pressure changes in a patient's esophagus and by adding conventional EKG electrodes for monitoring cardiac activity. In this way, tests for three of the main causes of chest pain can be conducted on an ambulatory patient, simultaneously with a single portable recorder. It should be understood that the concept of the malfunction monitor could be applied to a dual function monitor by eliminating one of the test systems and its associated test, or that it could be expanded to include additional tests.

The chest pain monitor 100 in the illustrated embodiment includes a pH probe 101 and a strain gauge probe 102, preferably a catheter tip strain gauge. The probes 101 and 102 are attached to a double cable 104 having one cable for the pH probe 101 and another cable for the strain gauge probe 102. A reference electrode 103 must be secured to the patient to obtain the pH reading as described previously. The size of the cable 104 and the probes 101, 102 should be minimized to permit insertion through a patient's nostril to their esophagus.

An EKG electrode 106, which may be an esophageal probe or a chest electrode, is also provided for monitoring cardiac activity.

Each of the sensors 101, 102 and 106 are input into a multiple channel portable recorder 108. The pH probe 101 must be interfaced with an amplifier/frequency modulator 110 as described above prior to recording. Similary, the strain gauge 102 must be interfaced with an amplifier/frequency modulator 111 to conver the stain gauge output signal into a recordable frequency modulated signal. The output signal of the EKG electrode 108 does not require interfacing prior to recording on tape recorder 108 such as a "Mini-Holter Recorder" which is designed specifically to monitor EKG activity.

After recording the data on magnetic tape, the tape is scanned on a high speed playback unit 114. The playback unit output on the pH channel and the strain gauge channel each being converted by amplifier/demodulator circuits 115 and 116. The EKG channel is connected to an EKG paper record printer 118 which is designed to clearly present arrhythmia data. The output signal of the amplifier/demodulator circuits 115 and 116 are supplied separately to a paper strip chart recorder 120 to create a visually perceptible record of reflux activity and esophageal spasm activity.

The gastroesophageal reflux monitor system of the present invention uses reliable and easy-to-use magnetic tapes as the recording medium. Magnetic tapes can be recorded on currently available miniature recording devices, which may be worn by a patient without interfering with normal daily activities.

The foregoing is a description of two embodiments of the present invention and should not be read in the restrictive sense but only as explaining the underlying concepts. The invention may be further developed within the scope of the following claims.

What is claimed is:

1. A gastroesophageal reflux monitor comprising:

a probe means for sensing a change in acidity which is adapted to be placed in a patient's esophagus;

a reference electrode adapted to be placed in contact with a patient's skin;

amplifier/frequency modulator means connected to the probe means and reference electrode for amplifying the voltage difference between the probe means and reference electrode and converting the voltage difference to a frequency modulated signal;

recorder means connected to the amplifier/frequency modulator means for recording the frequency modulated signal on a machine readable recording medium for a period of time;

playback means for scanning the recorded frequency modulated signal on the recording medium and providing a playback signal;

amplifier/frequency demodulator means for filtering, amplifying and converting the playback signal to an output voltage; and a display device responsive to the output voltage for creating a visually perceptible record of the sensed change in acidity of a patient's esophagus.

2. The gastroesophageal reflux monitor of claim 1 wherein said amplifier/frequency modulator means comprises:

a first amplifier connected to the probe means and reference electrode having a variable resistance feedback loop for calibrating said first amplifier to yield a first output voltage of a predetermined magnitude when the probe means is exposed to a solution of known high acidity;

a second amplifier connected to the first amplifier and having a variable resistance input for calibrating said second amplifier to yield a second output voltage of a predetermined magnitude when the probe means is exposed to a solution of known neutral pH; and a voltage to frequency convertor connected to the second amplifier which produces the frequency modulated signal which is related to the output voltage received from the second amplifier.

3. The gastroesophageal reflux monitor of claim 2 wherein said amplifier/frequency demodulator means comprises:

a filter and amplifier circuit means for receiving the playback signal from the playback means and providing an amplified frequency modulated signal;

a frequency demodulator circuit means for converting the amplified frequency modulated signal to said output voltage, which is related to the voltage difference between the probe means and the reference electrode; and, an output amplifier having offset and gain adjustment means for providing an amplified output voltage to the display device which accurately reflects the voltage difference between the probe means and the reference electrode.

4. The gastroesophageal reflux monitor of claim 3 wherein said display device is a strip chart recorder adapted to write a history on a paper strip chart.

5. The gastroesophageal reflux monitor of claim 2 wherein said amplifier/frequency modulator means further comprises:

calibration terminal means for connecting said amplifier/frequency modulator means to an electronic frequency meter or, alternatively, to a strip chart recorder through the demodulator means to permit monitoring of the frequency modulated signal during calibration;

reduction circuit means for reducing the frequency of the frequency modulated signal by a fixed ratio, equal to the ratio at playback to recorded speeds, to provide a reduced signal; and, recording terminal means for connecting the reduction circuit means of said amplifier/frequency modulator means to permit said recorder to record the reduced signal.

6. The gastroesophgeal reflux monitor of claim 5 wherein said playback means scans a tape at a rate of speed greater than the speed of said recorder, said rate of speed corresponding to the inverse of the fixed ratio of reduction by the reduction circuit means.

7. The gastroesophageal reflux monitor of claim 1 wherein said amplifier/frequency demodulator means comprises:

a filter and amplifier circuit means for receiving the playback signal from the playback means and providing an amplified frequency modulated signal;

a frequency demodulator circuit means for converting the amplified frequency modulated signal to said output voltage, which is related to the voltage difference between the probe means and the reference electrode; and an output amplifier having offset and gain adjustment means for providing an amplified output voltage to the display device which accurately reflects the voltage difference between the probe means and the reference electrode.

8. In a gastroesophgeal reflux monitor system having a probe means for electrically sensing the acidity of a person's esophagus, a skin electrode means for obtaining a reference voltage, a recording means for recording on a magnetic tape the sensed change in acidity over an extended period of time, a scanner means for playing back the magnetic tape, and a strip chart recorder means for writing on a paper strip chart a visually perceptible history of the sensed change in acidity the improvement comprising:

a first amplifier electrically connected to the probe means and reference electrode means and having a variable resistance feedback loop which calibrates the first amplifier thereby yielding a first specified output voltage when the probe means is exposed to a known high acidity level solution;

a second amplifier electrically connected to the first amplifier and having a variable resistance input which calibrates the second amplifier thereby yielding a second specified output voltage when the probe means is exposed to a solution of known neutral pH;

a voltage to frequency conversion circuit means electrically connected to the output of the second amplifier for producing a frequency output related to the output voltage received from the second amplifier;

a frequency reduction circuit means connected to the output of the voltage to frequency conversion circuit means for producing a reduced frequency output which is recorded by the recording means on the magnetic tape;

said scanner means being adapted to play back the magnetic tape at a faster speed than the recording speed to produce a scanner output having substantially the same frequency as the frequency output of the voltage to frequency conversion circuit means;

a filter and amplifier circuit means for receiving the scanner output from the scanner means and providing an amplified frequency modulated signal;

a frequency to voltage conversion circuit means for converting voltage of the second amplifier; and an output amplifier having offset and gain adjustment means for providing a signal to the strip chart recorder means, which accurately reflects the voltage difference between the probe means and the reference electrode means.

9. The gastroesophageal reflux monitor system of claim 8 further comprising:

a first terminal connected to the output of the voltage to frequency conversion circuit means;

a second terminal connected to the input of the frequency to voltage conversion circuit means;

means for connecting said first and second terminals; and a meter connected to the output of the frequency to voltage conversion circuit means for obtaining a real time reading whereby the system may be calibrated without using a strip chart recorder means or scanner means.

10. A gastroesophageal reflux monitor system comprising:

a probe means for yielding an output voltage related to the pH of a patient's esophagus;

an amplifier means electrically connected to the probe means for amplifying the voltage received from the probe means, and having means for adjusting gain and offset;

a frequency modulator means electrically connected to the amplifier means for converting the voltage received from the amplifier means to a frequency;

a recording means electrically connected to the modulator means for recording the output of the modulator means on a recording medium;

a scanner which reads the record of the frequency output from the recording medium;

a frequency demodulator means electrically connected to the scanner for converting the recorded frequency to a voltage output; and a display device electrically connected to the frequency demodulator means which converts the output thereof to a visually perceptible form for analysis of the change in pH in a patient's lower esophagus to contiunously monitor regurgitation of stomach contents into the esophagus over a period of time.

11. The gastroesophageal reflux monitor system of claim 10 wherein said frequency modulator means comprises an integrated circuit means for converting a variable voltage to a corresponding frequency, and having an output terminal connected through the demodulator means to a meter means for calibrating first and second operational amplifiers.

12. The gastroesophageal reflux monitor system of claim 11 wherein an output of the integrated circuit means for converting voltage to frequency is electrically connected to a frequency divider integrated circuit which is serially connected to the recording means whereby said recording means imparts to said recording medium a predetermined fraction of the frequency generated by the voltage to frequency integrated circuit means to permit calibration of the system at frequencies equal to those seen by the demodulator means during highspeed playback.

13. The gastroesophageal reflux monitor system of claim 12 wherein said frequency demodulator means comprises a frequency to voltage integrated circuit means for converting the frequency output of the scanner to a voltage signal.

14. The gastroesophageal reflux monitor system of claim 13 wherein said display device is a recorder adapted to translate the voltage signal from the frequency to voltage integrated circuit means to a marking on a paper strip chart.

15. The gastroesphageal reflux monitor system of claim 14 further comprising a terminal means connected to the output of the frequency demodulator means for providing a modified voltage to an electronic meter.

16. A multiple function monitor comprising:

first probe means for electrically sensing the relative acidity of a person's esophagus to provide a first output signal;

first probe interface means for converting the first output signal to a frequency modulated signal;

a second probe means for electrically sensing pressure changes in said person's esophagus to provide a second output signal;

a second probe interface means for converting the second output signal to a second frequency modulated signal;

electrode means for sensing cardiac activity of said person to provide a third signal;

recorder means having a plurality of channels for simultaneously recording all of said signals;

playback means for scanning the recorded signals to provide a set of discrete playback signals;

amplifier/demodulator means for filtering, amplifying and converting said set of discrete playback signals to a set of discrete playback output signals; and, a display device means responsive to the set of discrete playback output signals for creating discrete visually perceptible records of the sensed relative acidity of said person's esophagus, the sensed pressure changes in said person's esophagus, and the cardiac activity of the person.

* * * * *